United States Patent [19]

Cielo et al.

[11] Patent Number: 4,541,280

[45] Date of Patent: Sep. 17, 1985

[54] EFFICIENT LASER GENERATION OF SURFACE ACOUSTIC WAVES

[75] Inventors: Paolo G. Cielo, Montreal; Jean Bussière, St-Bruno, both of Canada

[73] Assignee: Canadian Patents & Development Ltd., Ottawa, Canada

[21] Appl. No.: 454,094

[22] Filed: Dec. 28, 1982

[51] Int. Cl.[4] ............................................. G01N 29/04
[52] U.S. Cl. ........................................ 73/603; 73/643; 73/662
[58] Field of Search ................. 73/603, 655, 656, 657, 73/643, 606, 662; 356/35.5; 350/358

[56] References Cited

U.S. PATENT DOCUMENTS 4,121,470 10/1978 Kaule ..................................... 73/643
4,169,662 10/1979 Kaule et al. .......................... 350/358

Primary Examiner—Anthony V. Ciarlante
Attorney, Agent, or Firm—Edward Rymek

[57] ABSTRACT

The surface acoustic waves are generated by laser beam that is focussed onto a surface to irradiate it in an arcuate pattern as a partial annulus or as a still or moving fringe pattern. The arcuate pattern may be formed by a transmitting or a reflecting axicon, while the fringe pattern may be formed by splitting the laser beam into two beams and directing the two beams to the surface. In addition, a lens or a frequency shifting device may be placed in the path of one of the split beams to form a circular fringe or a moving fringe, respectively.

12 Claims, 6 Drawing Figures

EFFICIENT LASER GENERATION OF SURFACE ACOUSTIC WAVES

BACKGROUND OF THE INVENTION

This invention is directed to ultrasonic techniques for detecting flaws on a surface, and in particular, to a method and laser apparatus for generating surface acoustic waves.

Conventional ultrasonic and eddy current techniques have been used for detecting flaws in various types of objects. However, these techniques require contact with the object and, therefore, cannot be used when non-contact is desirable or necessary, as with objects at high temperatures.

Non-contact techniques have been developed in which bulk acoustic waves are generated in a material by a laser and the acoustic waves reflected by the inner flaws are detected by interferometry. The generation of bulk acoustic waves is described by interferometry. The generation of bulk acoustic waves is described by W. Kaule et al in U.S. Pat. No. 4,121,469 which issued on Oct. 4, 1978; by R. L. Melcher et al in U.S. Pat. No. 4,137,991 which issued on Feb. 6, 1979; and by W. Kaule et al in U.S. Pat. No. 4,169,662 which issued on Oct. 2, 1979. The interferometric method of detecting acoustic waves in a material is described by C. M. Penney in U.S. Pat. No. 3,978,713 which issued on Sept. 7, 1976; and by E. Primback in U.S. Pat. No. 4,180,324, which issued on Dec. 25, 1979. This non-contact technique has the advantages of better repetitivity of the measurement because of the absence of a coupling liquid, ease of scanning, access to concave or irregular surfaces, and large and flat frequency response leading to an improved spatial and temporal resolution.

It has been found, however, that the detection of cracks or flaws in surfaces may best be carried out by using surface or Rayleigh acoustic waves, as described in the publication by B. R. Tittman et al, "Fatigue Lifetime Prediction with the Aid of Surface Acoustic Wave NDE", Journal N.D.E., 1, 123 (1980). Surface acoustic waves are difficult to generate by conventional piezoelectric methods, especially at high frequencies, because of precise angular alignment and need for a liquid couplant which strongly attenuates surface waves. The laser generation of surface acoustic waves has not been very successful to date as outlined in the publication by A. M. Aindow et al "Laser-Generated Ultrasonic Pulses at Free Metal Surfaces", J. Acoust. Soc. Am., 69, 449, 1981, because of low efficiency, low frequency and difficulty to discriminate against bulk waves.

SUMMARY OF THE INVENTION

It is therefore an object of this invention to provide a method and apparatus for efficiently producing surface acoustic waves using a laser beam.

This and other objects are achieved in a method for generating surface acoustic waves which comprises providing a laser generated optical beam, and directing the beam to the surface in order to irradiate it in an arcuate pattern.

In accordance with one aspect of the invention, the arcuate pattern may be obtained by focussing the beam into a partial or complete annulus on the surface by an axicon lens located on the beam path or by an axicon reflector for reflecting the beam to the surface.

In accordance with another aspect of the invention, the surface acoustic waves may be generated by an optical fringe pattern irradiated on the surface, the fringe pattern being formed from the laser beam which is split into two beams. In addition, a lens may be placed in the path of one of the split beams to form a circular fringe, or a frequency shifting element may be placed in the path of one of the split beams to form a moving fringe.

Many other objects and aspects of the invention will be clear from the detailed description of the drawings.

DETAILED DESCRIPTION

Figure 1:
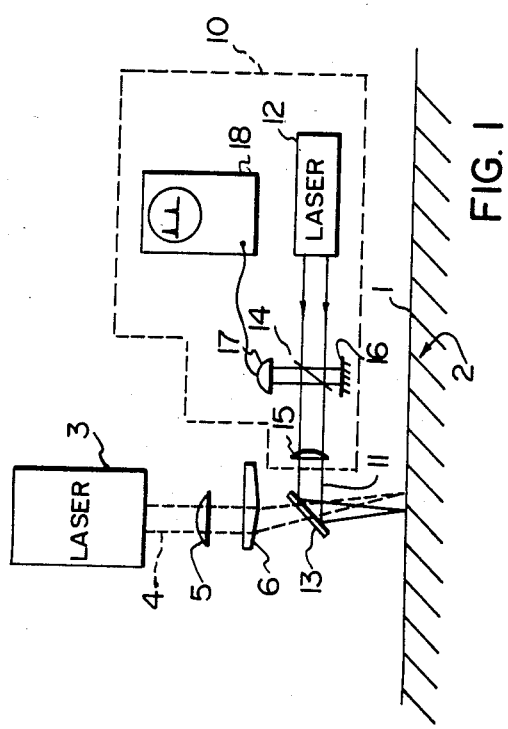
FIG. 1 illustrates apparatus for generating surface acoustic waves.
Figure 2:
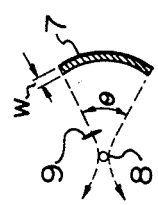
FIG. 2 illustrates the radiated area on the surface to be inspected.

FIG. 1 illustrates one embodiment by which a surface acoustic wave may be generated efficiently on the surface 1 of a material 2 that is to be inspected. The apparatus includes an infrared laser 3 that generates a coherent beam. Laser 3, which may be a Q-switched Nd:YAG laser, provides a pulsed beam 4 that is focussed by a lens 5 on the surface 1. In addition, an axicon 6 or conical lens is used to refract the beam 4 such that the focussed area has a partial annulus 7 subtending an angle $\theta$ and having a width w, as shown in FIG. 2.

In this method, a thermal-stress surface wave is produced by the absorption in the partial annulus 7 illuminated by the shaped laser pulse beam 4. This acoustic wave moves off to the right, expanding and dissipating. At the same time, a wave also moves off to the left where it converges to a narrow focal region 8, as illustrated by the dotted lines. Any bulk acoustic waves generated by the heated area 7 also diverge rapidly, resulting in acoustic echoes of very low power compared to the converging surface wave. The radius of the converging wave can be varied by moving the axicon 6 in a vertical direction towards or away from laser 3. On the other hand, a displacement of the axicon 6 in a horizontal direction into or out of the beam 4, will change the converging angle $\theta$. Large values of $\theta$, i.e. up to 360°, may be desirable when the orientation of a surface crack is not known and the surface is being scanned. Moreover, a large aperture $\theta$ implies better focussing of the acoustic wave, because of the diffraction laws. In generating surface acoustic wave, because of the diffraction laws. In generating surface acoustic waves in this manner, the average acoustic wavelength $\lambda$ is equal to twice the width w of the heated area. Width w for a Q-switched, single transverse mode Nd:YAG laser can be made in the order of 100 $\mu$m. This results in a cross-section of the focused surface wave of the order of 0.2 to 1 mm, depending on the value of the angle $\theta$. The increase in the efficiency, i.e. the increase of the amplitude of the detected signal with respect to the signal obtained by a conventional unfocussed technique is thus of the order of 100 if the radius of the converging acoustic wave is 1 cm.

The surface wave in the focal egion 8 may be detected by conventional interferometric techniques as illustrated in FIG. 1. This technique includes the use of a Michelson interferometer 10 which provides a probing beam 11 generated by a laser 12. The interferometer 10 further includes a beam splitter 14 which allows part of the laser 12 beam to pass through to a lens 15 to produce beam 11. The remaining part of the laser 12 beam is reflected to a mirror 16. The returning beams are directed to a detector 17 which produces a signal for the readout apparatus 18. Beam 11 is deflected by a dichroic mirror 13 to be focussed on the focal region 8 of the surface wave in order to take advantage of the large signal amplitude produced by the concentration of the acoustic wave in that region. The presence of a crack 9 in the path of the acoustic wave from its point of origin, area 7, will strongly reduce the amplitude of the detected signal in region 8 since the crack 9 would cause part of the surface wave to be reflected and another portion to be diffracted. Thus, cracks or flaws may be detected by scanning the surface 1 of material 2. In order to further increase the power of laser 12 and thus the signal to noise ratio of the system, laser 12 may be a diode laser that is pulsed in synchronism with laser 3.

Figure 3:
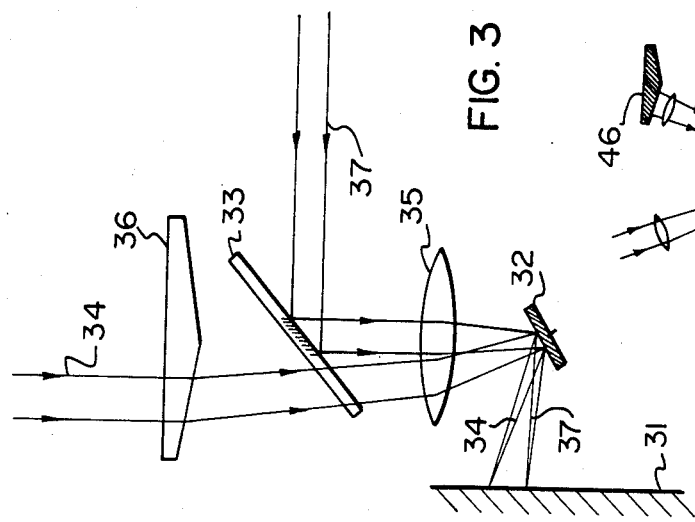
FIGS. 3 and 4 illustrate alternate apparatus for generating the focussed laser beam.

FIG. 3 illustrates an alternate embodiment of the surface wave generator in accordance with the present invention. Beam 34 passes through the axicon 36 and then through a partially reflecting mirror 33, a lens 35 and a rotating mirror 32 which reflects the focussed beam 34 onto the surface 31 to be inspected. The rotating mirror 32 allows the beam 34 to scan the surface 31. The interferomagnetic beam 37 is reflected by the mirror 33 through lens 35 and onto mirror 32 to scan beam 37 across the surface 31 in synchronism with beam 34.

Figure 4:
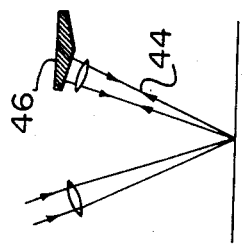

In a further embodiment shown in FIG. 4, the acoustic wave generating beam 44 is directed to a reflecting axicon 46 which produces the curved heated area.

The interferometric signal obtained from the above apparatus may be analysed simply for the detecting of cracks. On the other hand, more complex signal processing may be utilized. For instance, a spectroscopic analysis of the detected signal may be made taking advantage of the selective reflectivity by the crack of shorter acoustic wavelengths as well as time delay of the wave following the crack profile. Such an analysis is described by C. P. Burger et al, "Rayleigh Wave Spectroscopy to Measure the Depth of Surface Cracks", 13 Symposium NDE, San Antonio, April 1981. Similar techniques can be used to analyse dispersive surface features other than cracks. For example, the thickness of a coating can be evaluated from the phase delays of the different spectral components of the detected signal. Other possible applications are the measurement of the acoustic velocity and attenuation of the material.

Figure 5:
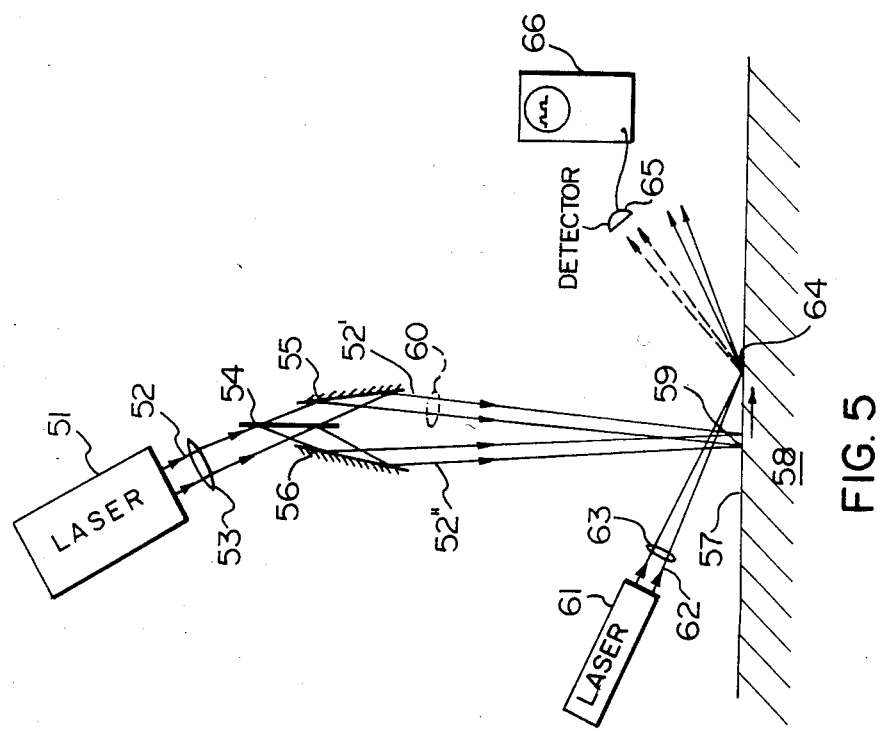
FIG. 5 illustrates a fringe method for generating surface acoustic waves.

The maximum frequency of the acoustic wave which can be generated by the method and apparatus described above is limited by the width w of the laser-heated area 7 to approximately 30 MHz. A narrower heated area 7 could be produced by increasing the aperture of the optical system, but this would make scanning more difficult. High-frequency acoustic waves may be required in some cases, such as when thin cracks must be detected, or thin coatings must be inspected. These high frequency surface acoustic waves may be generated efficiently in the apparatus illustrated in FIG. 5. A laser 51 generates a beam 52, which is focussed by a lens 53 onto a beam splitter 54 that produces beams 52' and 52" which are reflected by mirrors 55 and 56 onto the surface 57 of the material 58 being tested. The beams 52' and 52" are directed to the same irradiated region 59 in order to obtain an interference fringe on the surface 57 of the material 58. An optional lens 60 is positioned in the path of beam 52' such that circular fringes occur which will produce a converging surface wave travelling towards a probing spot in region 59. In addition, laser 51 is amplitude modulated with a period $T_{ac}$ following the resonance condition $v = \lambda_{ac}/T_{ac}$ where $v$ is the surface-acoustic-wave phase velocity and $\lambda_{ac}$ is the surface acoustic wavelength which is equal to the interfringe of the fringe pattern. Typical values for a mode-locked laser 51 and a metallic surface are $T_{ac} = 5$ nsec and $\lambda_{ac} = 15$ μm, which correspond to a frequency of the surface acoustic wave of 200 MHz.

The probing system could be similar to the one described with respect to FIG. 1, if the electronics of the interferometer 10 are sufficiently fast. Another probing technique, which is also well known in the literature, may be used as shown schematically in FIG. 5. The probing laser 61 beam 62 is focussed by a lens 63 onto a probing area 64 which is larger than $\lambda_{ac}$. Beam 62 is diffracted by the surface-wave train as it moves through area 64 towards a detector 65 with its readout 66. This probing technique relaxes the electronics speed requirements, but it has a lower temporal resolution and requires a smoother surface than the probing technique described with respect to FIG. 1.

The fringe generating method of generating surface acoustic waves is more complex and more difficult to scan than the earlier described focussing method, however, it is potentially more efficient because very little power is coupled to bulk acoustic waves. The resonance condition $V = \lambda_{ac}/T_{ac}$ can be satisfied either for the surface waves or for the bulk waves but not for both, because these two kinds of waves have different velocities and wavelengths. Thus, nearly 50% of the acoustic power goes into each of the counter-propagating surface waves, providing a higher signal together with a lower spurious acoustic noise.

Figure 6:
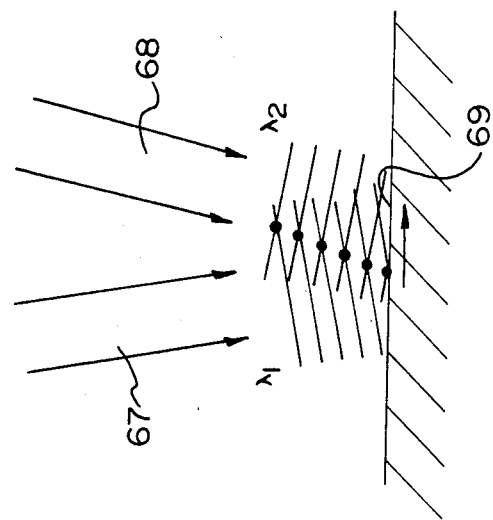
FIG. 6 illustrates a method for producing a moving fringe.

An even larger coupling efficiency is possible by eliminating the counter-propagating surface wave. This can be done by scanning the fringe pattern on the surface 57 to be inspected at the same speed as the surface wave velocity. This would require a mirror rotating at very high speed in order to follow the acoustic wave which travels at a speed in the order of 3,000 m/sec on the surface. Alternately as shown in FIG. 6, two interfering beams 67 and 68 of different frequencies may be used to obtain a displacement of the interference fringes within the laser-irradiated region 69 without any physically moving parts. The two coherent beams 67, 68, of frequencies $\lambda_1$ and $\lambda_2$, respectively, are superposed on the surface 69 so as to produce an interference fringe pattern. If $\lambda_2 > \lambda_1$ the intersection between the wavefronts, which corresponds to the position of a bright fringe, moves towards the right as the wave progresses, as can be seen in FIG. 6. If the speed of the bright fringe is the same as the velocity of the acoustic wave, a single acoustic wave propagating towards the right will be generated. This condition can be written: $f_{ac}/f_{op} = (\lambda_2 - \lambda_1)/\lambda_1$, where $f_{ac}$ is the frequency of the acoustic wave and $f_{op}$ is the frequency of the optical wave. Typical values are $f_{op} = 3 \cdot 10^{14}$ Hz and $f_{ac} = 5 \cdot 10^7$ Hz, which gives an interfringe $\lambda_{ac} = 60$ μm and a wavelength shift $(\lambda_2 - \lambda_1)/\lambda_1 = 1.7 \cdot 10^{-7}$. This can be obtained, for example, by shifting the frequency of one of the two beams 52′,52″ with a Bragg cell inserted in the path of one of the beams 52′, 52″. A typical Bragg cell with a carrier frequency of 50 MHz would be suitable.

The above methods of generating surface acoustic waves provide many advantages. For example, they provide (1) an increased optical detectability because of the self-amplification of the convergent surface acoustic wave as well as highly efficient fringe generation of the surface wave; (2) a reduced acoustic noise because of the enhancement of the surface wave signal together with a reduction of the coupling efficiency to spurious bulk acoustic waves; (3) an increased resolution because of the narrow cross-section of the focussed acoustic wave; and (4) a reduced heating of the laser-irradiated surface because of the relatively large heated surface with respect to cross-section of the focussed acoustic wave.

Many modifications in the above described embodiments of the invention can be carried out without departing from the scope thereof and therefore the scope of the present invention is intended to be limited only by the appended claims.

We claim:

1. A method of generating surface acoustic waves on a surface comprising:
    providing a laser generated optical beam;
    directing the beam to the surface;
    and focusing the beam into an annulus irradiated pattern on the surface to form a converging surface wave.

2. A method as claimed in claim 1 in which the annulus is a partial annulus.

3. Apparatus for generating acoustic surface waves on a surface comprising:
    laser means for generating a coherent beam of optical energy; and
    means for focusing the beam onto the surface in an annulus irradiated pattern to form a converging surface wave.

4. Apparatus as claimed in claim 3 wherein the annulus pattern is a partial annulus.

5. Apparatus as claimed in claim 3 or 4 wherein the focusing means includes an axicon lens located on the beam path.

6. Apparatus as claimed in claim 3 or 4 wherein the focusing means includes an axicon reflector for reflecting the beam to the surface.

7. A method of generating acoustic waves on a surface comprising:
    providing a laser generated optical beam;
    splitting the beam into two beams;
    directing the beams to the surface; and
    focusing the beams to form a fringe pattern on the surface to form a converging surface wave.

8. A method as claimed in claim 7 which includes:
    shifting the frequency of one of the two beams such that the fringe pattern moves on the surface.

9. Apparatus for generating acoustic surface waves on a surface comprising:
    laser means for generating a coherent beam of optical energy;
    beam splitter means for splitting the beam into two beams; and
    reflector means for deflecting the two beams onto the surface to form a fringe pattern on the surface to form a converging surface wave.

10. Apparatus as claimed in claim 9 which further includes a lens located in the path of one of the two beams.

11. Apparatus as claimed in claim 10 which further includes frequency shifting means located in the path of one of the two beams.

12. Apparatus as claimed in claim 9 which further includes frequency shifting means located in the path of one of the two beams.

* * * * *